US010340867B2

(12) United States Patent
Singh et al.

(10) Patent No.: US 10,340,867 B2
(45) Date of Patent: Jul. 2, 2019

(54) AMPLIFIER WITH BUILT IN TIME GAIN COMPENSATION FOR ULTRASOUND APPLICATIONS (71) Applicant: Butterfly Network, Inc., Guilford, CT (US)

(72) Inventors: Amandeep Singh, Jersey City, NJ (US); Kailiang Chen, Branford, CT (US); Tyler S. Ralston, Clinton, CT (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 16/245,202

(22) Filed: Jan. 10, 2019

(65) Prior Publication Data
US 2019/0149110 A1 May 16, 2019

Related U.S. Application Data (63) Continuation of application No. 16/011,755, filed on Jun. 19, 2018.
(Continued)

(51) Int. Cl.
*H03F 3/45* (2006.01)
*G01S 7/523* (2006.01)
(Continued)

(52) U.S. Cl.
CPC ....... *H03F 3/45179* (2013.01); *B06B 1/0223* (2013.01); *G01H 17/00* (2013.01); *G01N 29/4463* (2013.01); *G01S 7/523* (2013.01); *G01S 15/89* (2013.01); *H03M 1/12* (2013.01); *H03F 2200/129* (2013.01);
(Continued)

(58) Field of Classification Search
CPC .......... H03F 3/45179; H03F 2200/129; H03F 2203/45524; H03F 2200/294; G01H 17/00; G01N 29/4463; B06B 1/0223; H03M 1/12; H03M 1/124; G01S 15/89; G01S 7/523
See application file for complete search history.

(56) References Cited

U.S. PATENT DOCUMENTS

| 4,417,496 A | 11/1983 | Machanian |
| 4,829,491 A | 5/1989 | Saugeon et al. |

(Continued)

FOREIGN PATENT DOCUMENTS

| CN | 103607130 A | 2/2014 |
| TW | 201445554 A | 12/2014 |
| WO | WO 2007/096636 A1 | 8/2007 |

OTHER PUBLICATIONS

International Search Report and Written Opinion dated Feb. 7, 2017 for Application No. PCT/US2016/064314.
(Continued)

*Primary Examiner* — Daniel Pihulic
(74) *Attorney, Agent, or Firm* — Wolf, Greenfield & Sacks, P.C.

(57) ABSTRACT

An ultrasound circuit comprising a trans-impedance amplifier (TIA) with built-in time gain compensation functionality is described. The TIA is coupled to an ultrasonic transducer to amplify an electrical signal generated by the ultrasonic transducer in response to receiving an ultrasound signal. The TIA is, in some cases, followed by further analog and digital processing circuitry.

21 Claims, 7 Drawing Sheets

Related U.S. Application Data (60) Provisional application No. 62/522,622, filed on Jun. 20, 2017.

(51) Int. Cl.
*G01S 15/89* (2006.01)
*H03M 1/12* (2006.01)
*B06B 1/02* (2006.01)
*G01H 17/00* (2006.01)
*G01N 29/44* (2006.01)

(52) U.S. Cl.
CPC .............. *H03F 2200/294* (2013.01); *H03F 2203/45524* (2013.01); *H03M 1/124* (2013.01)

(56) References Cited

U.S. PATENT DOCUMENTS

| | | | |
|---|---|---|---|
| 5,844,445 | A | 12/1998 | Takeyari |
| 6,356,152 | B1 | 3/2002 | Jezdic et al. |
| 6,404,281 | B1 | 6/2002 | Kobayashi |
| 7,313,053 | B2 | 12/2007 | Wodnicki |
| 7,449,958 | B1 | 11/2008 | Voo |
| 7,605,660 | B1 | 10/2009 | Kobayashi |
| 8,662,395 | B2 | 3/2014 | Melandso et al. |
| 8,852,103 | B2 | 10/2014 | Rothberg et al. |
| 9,229,097 | B2 | 1/2016 | Rothberg et al. |
| 9,473,136 | B1 | 10/2016 | Chen et al. |
| 9,492,144 | B1 | 11/2016 | Chen et al. |
| 9,521,991 | B2 | 12/2016 | Rothberg et al. |
| 9,592,030 | B2 | 3/2017 | Rothberg et al. |
| 9,705,518 | B2 | 7/2017 | Chen et al. |
| 9,933,516 | B2 | 4/2018 | Chen et al. |
| 9,958,537 | B2 | 5/2018 | Chen et al. |
| 10,014,871 | B2 | 7/2018 | Chen et al. |
| 10,082,488 | B2 | 9/2018 | Chen et al. |
| 10,082,565 | B2 | 9/2018 | Chen et al. |
| 10,231,713 | B2 * | 3/2019 | Chen .................. A61B 8/56 |
| 2007/0001764 | A1 | 1/2007 | Huang et al. |
| 2007/0242567 | A1 | 10/2007 | Daft et al. |
| 2007/0287923 | A1 | 12/2007 | Adkins et al. |
| 2009/0250729 | A1 | 10/2009 | Lemmerhirt et al. |
| 2010/0063399 | A1 | 3/2010 | Walker et al. |
| 2010/0152587 | A1 | 6/2010 | Haider et al. |
| 2010/0237807 | A1 | 9/2010 | Lemmerhirt |
| 2010/0317972 | A1 | 12/2010 | Baumgartner et al. |
| 2011/0130109 | A1 | 6/2011 | Ogasawara |
| 2012/0206150 | A1 | 8/2012 | Holzer |
| 2012/0313701 | A1 | 12/2012 | Khlat et al. |
| 2013/0064043 | A1 | 3/2013 | Degertekin et al. |
| 2014/0107486 | A1 | 4/2014 | Kaplan et al. |
| 2014/0240482 | A1 | 8/2014 | Ikeda et al. |
| 2014/0288428 | A1 | 9/2014 | Rothberg et al. |
| 2015/0032002 | A1 | 1/2015 | Rothberg et al. |
| 2015/0145597 | A1 | 5/2015 | Huang et al. |
| 2015/0297193 | A1 | 10/2015 | Rothberg et al. |
| 2015/0374335 | A1 | 12/2015 | Brown et al. |
| 2016/0228099 | A1 | 8/2016 | Matsumura |
| 2016/0249882 | A1 | 9/2016 | Degertekin et al. |
| 2016/0287870 | A1 | 10/2016 | Yip et al. |
| 2017/0143306 | A1 | 5/2017 | Rothberg et al. |
| 2017/0160239 | A1 | 6/2017 | Chen et al. |
| 2017/0160387 | A1 | 6/2017 | Chen et al. |
| 2017/0160388 | A1 | 6/2017 | Chen et al. |
| 2017/0163225 | A1 | 6/2017 | Chen et al. |
| 2017/0163276 | A1 | 6/2017 | Chen et al. |
| 2017/0202541 | A1 | 7/2017 | Ralston |
| 2017/0264307 | A1 | 9/2017 | Chen et al. |
| 2017/0307739 | A1 | 10/2017 | Chen et al. |
| 2018/0070925 | A1 * | 3/2018 | Chen .................. A61B 8/56 |
| 2018/0210073 | A1 | 7/2018 | Chen et al. |
| 2018/0360426 | A1 | 12/2018 | Singh et al. |
| 2018/0361431 | A1 | 12/2018 | Singh et al. |
| 2018/0367110 | A1 * | 12/2018 | Singh ................. H03F 3/45179 |
| 2018/0367111 | A1 * | 12/2018 | Singh ................. H03F 3/45179 |

OTHER PUBLICATIONS

International Preliminary Report on Patentability dated Jun. 14, 2018 in connection with International Application No. PCT/US2016/064314.

International Search Report and Written Opinion dated Aug. 30, 2018 in connection with International Application No. PCT/US2018/038147.

International Search Report and Written Opinion dated Sep. 6, 2018 in connection with International Application No. PCT/US2018/038180.

International Search Report and Written Opinion dated Sep. 11, 2018 in connection with International Application No. PCT/US2018/038148.

Taiwanese Office Action dated Jan. 19, 2018 in connection with Taiwanese Application No. 105139662.

Agarwal et al., Single-Chip Solution for Ultrasound Imaging Systems: Initial Results. 2007 IEEE Ultrasonics Symposium. Oct. 1, 2007;1563-6.

Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012;173-6.

Cheng et al., An Efficient Electrical Addressing Method Using Through-Wafer Vias for Two-Dimensional Ultrasonic Arrays. 2000 IEEE Ultrasonics Symposium. 2000;2:1179-82.

Cheng et al., CMUT-in-CMOS ultrasonic transducer arrays with on-chip electronics. Transducers 2009. IEEE. Jun. 21, 2009;1222-5.

Cheng et al., Electrical Through-Wafer Interconnects with Sub-PicoFarad Parasitic Capacitance. 2001 Microelectromechan Syst Conf. Aug. 24, 2001;18-21.

Daft et al., A Matrix Transducer Design with Improved Image Quality and Acquisition Rate. 2007 IEEE Ultrasonics Symposium. Oct. 1, 2007;411-5.

Daft et al., Microfabricated Ultrasonic Transducers Monolithically Integrated with High Voltage Electronics. 2004 IEEE Ultrasonics Symposium. Aug. 23, 2004;1:493-6.

Doody et al., Modeling and Characterization of CMOS-Fabricated Capacitive Micromachined Ultrasound Transducers. J Microelectromechan Sys. Feb. 2011;20(1):104-118.

Gurun et al., Front-end CMOS electronics for monolithic integration with CMUT arrays: circuit design and initial experimental results. Proc Ultrason Symp. 2008;390-3.

Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. doi:10.1109/IEMBS.2010.5627580. Epub Dec. 6, 2010. 13 pages.

Kim et al., Design and Test of a Fully Controllable 64x128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

Kupnik et al., Wafer-bonded CMUT meets CMOS. MEMS-based Ultrasonic Transducer Arrays including Electronics Integration. 2010 CMOS Emerging Technology Workshop. Whistler, Canada. May 21, 2010. 22 pages.

Orozco, Programmable-Gain Transimpedance Amplifiers Maximize Dynamic Range in Spectroscopy Systems. Analog Dialogue. May 2013;47(05):1-5.

* cited by examiner

AMPLIFIER WITH BUILT IN TIME GAIN COMPENSATION FOR ULTRASOUND APPLICATIONS

CROSS-REFERENCE TO RELATED APPLICATIONS

This Application is a Continuation claiming the benefit under 35 U.S.C. § 120 of U.S. application Ser. No. 16/011,755, filed Jun. 19, 2018, and entitled "AMPLIFIER WITH BUILT IN TIME GAIN COMPENSATION FOR ULTRASOUND APPLICATIONS," which is hereby incorporated herein by reference in its entirety.

U.S. application Ser. No. 16/011,755 claims the benefit under 35 USC § 119(e) of U.S. Provisional Patent Application Ser. No. 62/522,622, filed Jun. 20, 2017, and entitled "AMPLIFIER WITH BUILT IN TIME GAIN COMPENSATION FOR ULTRASOUND APPLICATIONS," which is hereby incorporated herein by reference in its entirety.

BACKGROUND

Field

The present application generally relates to ultrasound devices having an amplifier for amplifying received ultrasound signals.

Related Art

Ultrasound probes include one or more ultrasound sensors which sense ultrasound signals and produce corresponding electrical signals. The electrical signals are processed in the analog or digital domain. Sometimes, ultrasound images are generated from the processed electrical signals.

BRIEF SUMMARY

According to an aspect of the present application, an ultrasound apparatus is provided, comprising an ultrasound sensor and a trans-impedance amplifier (TIA) coupled to the ultrasound sensor and configured to receive and amplify an output signal from the ultrasound sensor. The TIA may include time gain compensation (TGC) functionality, and thus the ultrasound device may lack a distinct TGC circuit downstream in the analog signal processing chain. While a TIA is one example of a suitable amplifier, other types of amplifiers may be used, such as low noise amplifiers (LNAs) or trans-conductance amplifiers.

According to an aspect of the present application, an ultrasound apparatus is provided, comprising an ultrasonic transducer to provide an analog electrical signal, and an amplifier having time gain compensation (TGC) functionality coupled to the ultrasonic transducer and configured to receive and amplify the analog electrical signal by a time-dependent amount.

According to an aspect of the present application, an ultrasound circuit is provided, comprising an ultrasound transducer, an analog signal processing chain coupled to the ultrasonic transducer, and an analog-to-digital converter (ADC), wherein the analog signal processing chain is coupled electrically between the ultrasonic transducer and the ADC, wherein the analog signal processing chain includes a combined trans-impedance amplifier (TIA) and time gain compensation (TGC) circuit.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Aspects of the disclosure relate to amplification circuitry for an ultrasound device. An ultrasound device may include one or more ultrasonic transducers configured to receive ultrasound signals and produce electrical output signals. Thus, the ultrasonic transducers may be operated as ultrasound sensors. The ultrasound device may include one or more amplifiers for amplifying the electrical output signals. In some embodiments, the amplifier(s) may be a trans-impedance amplifier (TIA) and may include time gain compensation (TGC) functionality. Analog processing stages (alternatively referred to herein as "blocks" or "components") may follow the TIA to perform various analog processing functions, such as averaging electrical signals produced by multiple TIAs of the ultrasound device. In at least some embodiments, the ultrasound device lacks a distinct TGC stage or circuit downstream of the TIA. While a TIA represents one example of a suitable amplifier type, other types of amplifiers may alternatively be employed, including LNAs or trans-conductance amplifiers.

According to an aspect of the present application, a method of processing ultrasound signals is provided. The method comprises generating an electrical signal using an ultrasonic transducer followed by amplifying and time gain compensating the electrical signal with a TIA, LNA, trans-conductance amplifier, or other suitable amplifier. For simplicity of discussion, a TIA is explicitly described here. In some embodiments, multiple TIAs are provided, and further processing comprises averaging the signals provided by multiple TIAs. The averaged signal may then be digitized by a suitable analog-to-digital converter (ADC). In some implementations, multiple TIAs (or other amplifiers) are provided, and further processing comprises using cross-coupled switches to flip the polarity of some signals to enable coded reception, such as the use of Hadamard coding.

The aspects and embodiments described above, as well as additional aspects and embodiments, are described further below. These aspects and/or embodiments may be used individually, all together, or in any combination of two or more, as the application is not limited in this respect.

Figure 1:
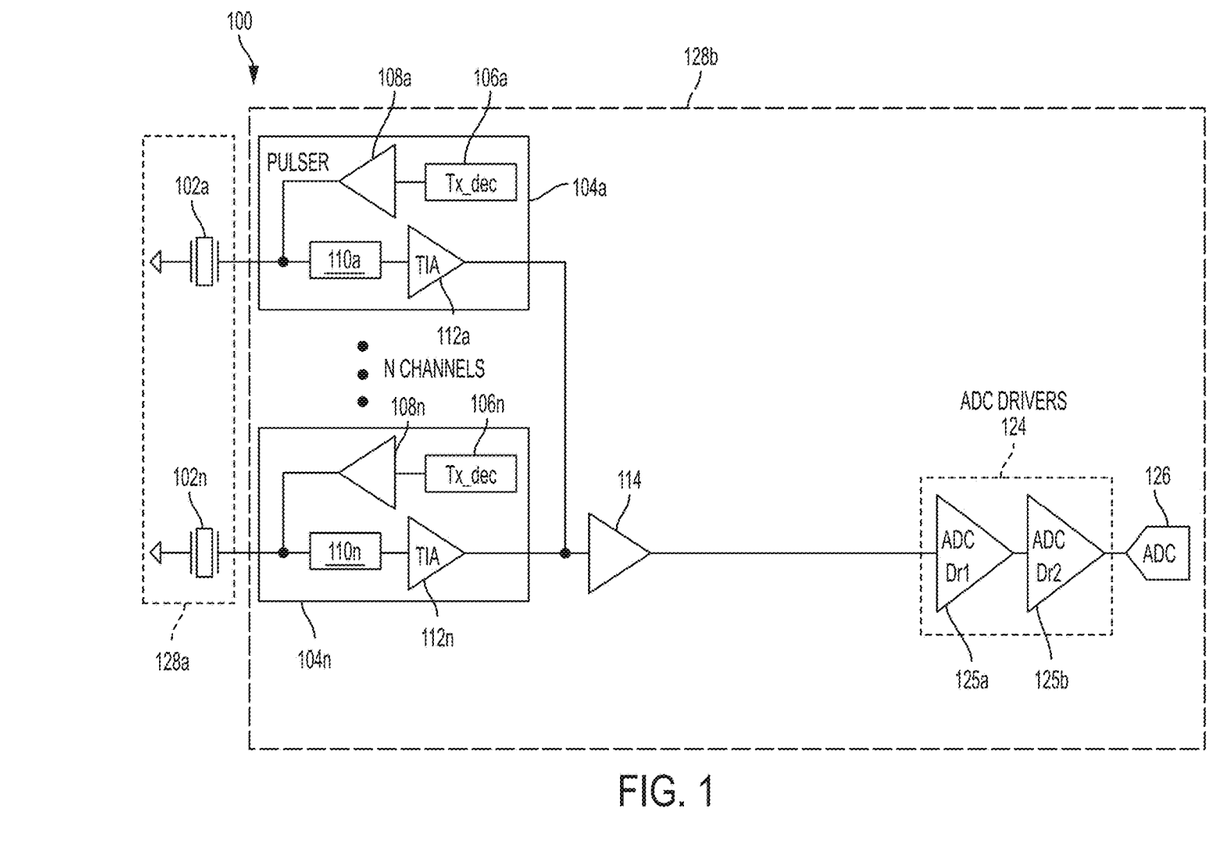
FIG. 1 is a block diagram of an ultrasound device including an amplifier for amplifying an ultrasound signal, according to a non-limiting embodiment of the present application.

FIG. 1 illustrates a circuit for processing received ultrasound signals, according to a non-limiting embodiment of the present application. The circuit 100 includes N ultrasonic transducers 102a . . . 102n, wherein N is an integer. The ultrasonic transducers are sensors in some embodiments, producing electrical signals representing received ultrasound signals. The ultrasonic transducers may also transmit ultrasound signals in some embodiments. The ultrasonic transducers may be capacitive micromachined ultrasonic transducers (CMUTs) in some embodiments. The ultrasonic transducers may be piezoelectric micromachined ultrasonic transducers (PMUTs) in some embodiments. Alternative types of ultrasonic transducers may be used in other embodiments.

The circuit 100 further comprises N circuitry channels 104a . . . 104n. The circuitry channels may correspond to a respective ultrasonic transducer 102a . . . 102n. For example, there may be eight ultrasonic transducers 102a . . . 102n and eight corresponding circuitry channels 104a . . . 104n. In some embodiments, the number of ultrasonic transducers 102a . . . 102n may be greater than the number of circuitry channels.

The circuitry channels 104a . . . 104n may include transmit circuitry, receive circuitry, or both. The transmit circuitry may include transmit decoders 106a . . . 106n coupled to respective pulsers 108a . . . 108n. The pulsers 108a . . . 108n may control the respective ultrasonic transducers 102a . . . 102n to emit ultrasound signals.

The receive circuitry of the circuitry channels 104a . . . 104n may receive the (analog) electrical signals output from respective ultrasonic transducers 102a . . . 102n. In the illustrated example, each circuitry channel 104a . . . 104n includes a respective receive circuit 110a . . . 110n and an amplifier 112a . . . 112n. The receive circuit 110a . . . 110n may be controlled to activate/deactivate readout of an electrical signal from a given ultrasonic transducer 102a . . . 102n. An example of suitable receive circuits 110a . . . 110n are switches. That is, in one embodiment the receive circuits are controllable switches which are switched during transmit mode to disconnect the ultrasonic transducers from the receive circuitry and during receive mode to connect the ultrasonic transducers to the receive circuitry. Alternatives to a switch may be employed to perform the same function.

The amplifiers 112a . . . 112n may be TIAs with built-in TGC functionality in some embodiments, outputting amplified and time gain compensated analog signals. The use of TIAs with built-in TGC functionality may facilitate low power operation of the circuit 100 compared to use of alternative amplifier designs. Also, the use of a TIA with built-in TGC functionality may allow for omission of any downstream TGC stages or circuits, which may further aid in power reduction.

The circuit 100 further comprises an averaging circuit 114, which is also referred to herein as a summer or a summing amplifier. In some embodiments, the averaging circuit 114 is a buffer or an amplifier. The averaging circuit 114 may receive output signals from one or more of the amplifiers 112a . . . 112n and may provide an averaged output signal. The averaged output signal may be formed in part by adding or subtracting the signals from the various amplifiers 112a . . . 112n. The averaging circuit 114 may include a variable feedback resistance. The value of the variable feedback resistance may be adjusted dynamically based upon the number of amplifiers 112a . . . 112n from which the averaging circuit receives signals. In some embodiments, the variable resistance may include N resistance settings. That is, the variable resistance may have a number of resistance settings corresponding to the number of circuitry channels 104a . . . 104n. Thus, the average output signal may also be formed in part by application of the selected resistance to the combined signal received at the inputs of the averaging circuit 114.

In some embodiments, the averaging circuit 114 also includes built-in TGC functionality. Such functionality may expand on the TGC function performed by the amplifiers 112, and thus may further facilitate omission of a distinct downstream TGC circuit. Any suitable TGC circuitry may be included in the averaging circuit 114.

The averaging circuit 114 is coupled to an ADC 126 via ADC drivers 124. As should be appreciated from FIG. 1, in some embodiments the output terminal of the averaging circuit is directly coupled to the ADC drivers, without intervening processing stages. In the illustrated example, the ADC drivers 124 include a first ADC driver 125a and a second ADC driver 125b. The ADC 126 digitizes the signal(s) from the averaging circuit 114.

While FIG. 1 illustrates a number of components as part of a circuit of an ultrasound device, it should be appreciated that the various aspects described herein are not limited to the exact components or configuration of components illustrated. For example, aspects of the present application relate to the amplifiers 112a . . . 112n, and the components illustrated downstream of those amplifiers in circuit 100 are optional in some embodiments.

The components of FIG. 1 may be located on a single substrate or on different substrates. For example, as illustrated, the ultrasonic transducers 102a . . . 102n may be on a first substrate 128a and the remaining illustrated components may be on a second substrate 128b. The first and/or second substrates may be semiconductor substrates, such as silicon substrates. In an alternative embodiment, the components of FIG. 1 may be on a single substrate. For example, the ultrasonic transducers 102a . . . 102n and the illustrated circuitry may be monolithically integrated on the same die (e.g., a semiconductor die, such as silicon). Such integration may be facilitated by using CMUTs as the ultrasonic transducers.

According to an embodiment, the components of FIG. 1 form part of an ultrasound probe. The ultrasound probe may be handheld. In some embodiments, the components of FIG. 1 form part of an ultrasound patch configured to be worn by a patient or part of an ultrasound pill to be swallowed by a patient.

Figure 2:
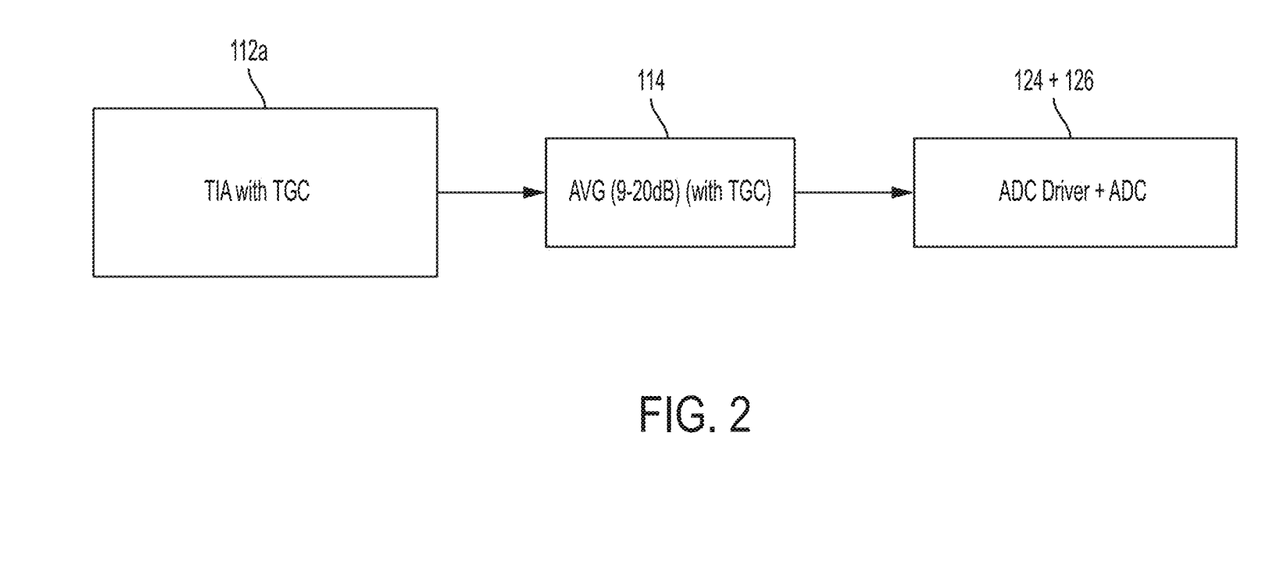
FIG. 2 illustrates an ultrasound signal receive circuitry chain including a trans-impedance amplifier (TIA) with time gain compensation (TGC) functionality and a plurality of analog signal processing stages following the TIA, according to a non-limiting embodiment of the present application.

FIG. 2 illustrates an ultrasound signal receive circuitry chain including a TIA with time gain compensation (TGC) functionality and a plurality of analog signal processing stages following the TIA, according to a non-limiting embodiment of the present application. FIG. 2 includes amplifier 112a, averaging circuit 114, ADC driver 124, and ADC 126, the latter two of which are illustrated as a single block for ease of explanation.

In some implementations, the amplifier 112a is a TIA with built-in TGC functionality, outputting amplified and time gain compensated analog signals. integrating TGC functionality into amplifier 112a may facilitate low power operation of the circuit 100 compared to use of alternative amplifier designs. The use of an amplifier 112a with built-in TGC functionality may allow for omission of any downstream TGC stages or circuits, as is the case in FIG. 2, which may further aid in power reduction and design simplification. The amplifier 112a receives an electrical signal representing an ultrasound signal received by the ultrasound transducer. The amplifier 112a applies at least a minimal gain to the electrical signal as part of TIA functionality. Additionally, amplifier 112a will provide an additional, time dependent amount of gain representing TGC functionality to compensate for attenuation of signals.

The gain provided by the illustrated TIA with TGC functionality may assume any suitable values. For example, the gain from the TIA functionality may be on the order of 90 decibels (e.g., between 50 and 100 dB) and the gain from TGC functionality may be a fraction of that (e.g., from zero to 18 dB, or any other suitable value). Thus, as a non-limiting example, the total gain provided by the illustrated TIA with TGC functionality may range significantly depending on the point in time of reception of the ultrasound signal. As one example, the gain may range between 90 and 108 dB during reception of a signal.

While FIG. 2 illustrates TIA 112a, it should be appreciated that any of the TIAs 112a ... 112n may have the configuration shown in FIG. 2.

The averaging circuit 114 receives the output of the amplifiers 112a ... 112n. In some embodiments, the averaging circuit may improve the ultrasound signal to noise ratio and/or may provide TGC functionality. As a non-limiting example, the averaging circuit provides between 5 dB and 20 dB (e.g., a 9 dB) improvement to the signal to noise ratio and up to an additional 10-20 dB (e.g., 11 dB) of TGC. The averaging circuit 114 is coupled to an ADC 126 via ADC drivers 124. As should be appreciated from FIG. 1, in some embodiments the output terminal of the averaging circuit is directly coupled to the ADC drivers, without intervening processing stages. The ADC 126 digitizes the signal(s) from the averaging circuit 114.

Figure 3:
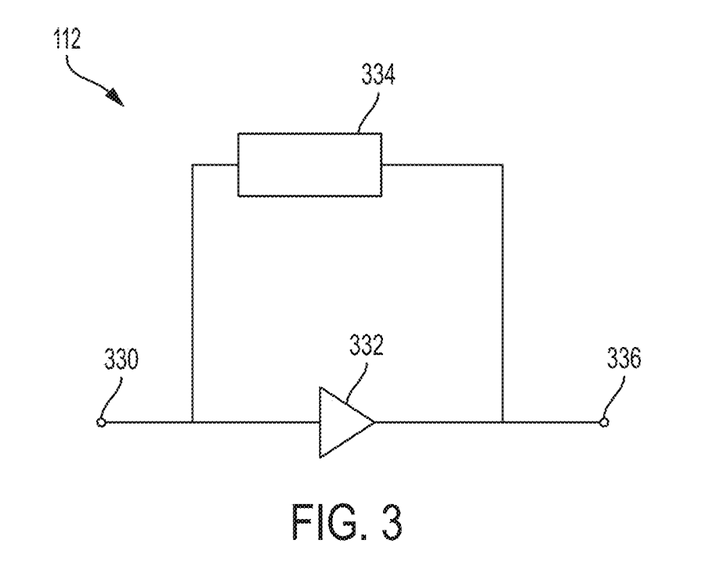
FIG. 3 is a block diagram of a TIA with TGC functionality, according to a non-limiting embodiment of the present application.

FIG. 3 is a block diagram of a TIA with TGC functionality (e.g. one of the amplifiers 112a ... 112n), according to a non-limiting embodiment of the present application. FIG. 3 includes input terminal 330, amplifier 332, output terminal 336, and variable impedance feedback circuit 334. The input terminal 330 receives analog electrical signals representing ultrasound signals. In some implementations, the input terminal 330 is in electrical communication with an ultrasound transducer, e.g. any one of the transducers 102a ... 102n, either through a direct coupling or through a switch, e.g. any one of the switches 110a ... 110n.

The signals received at the input terminal 330 are amplified by the amplifier 332. The amount of gain may be selected to provide sufficient dynamic range for subsequent processing and digitization of the signal output at output terminal 336. In some implementations, the amplifier will provide a gain between 90 dB and 120 dB, as a non-limiting example. In sonic implementations, the amount of gain is dynamically varied over time to provide TGC that compensates for ultrasound signal attenuation.

The signal at output terminal 336 is fed back to the input terminal 330 of the amplifier 332 through the variable impedance feedback circuit 334, which is used to modify the gain of TIA 112. Variable impedance feedback circuit 334 may be configured to generate—using timing circuitry or otherwise—or alternatively to receive—from a digital controller, processor, or other source—one or more control signals that dynamically adjust the feedback impedance seen by amplifier 332 in order to provide a time-varying amount of gain that can be used to provide TGC functionality. In some implementations, amplifier 332 may be an amplifier besides a TIA, such as a low noise amplifier (LNA) or trans-conductance amplifier. In some implementations, amplifier 332 may be a voltage amplifier and input terminal 330 may be connected to a piezoelectric transducer.

Figure 4A:
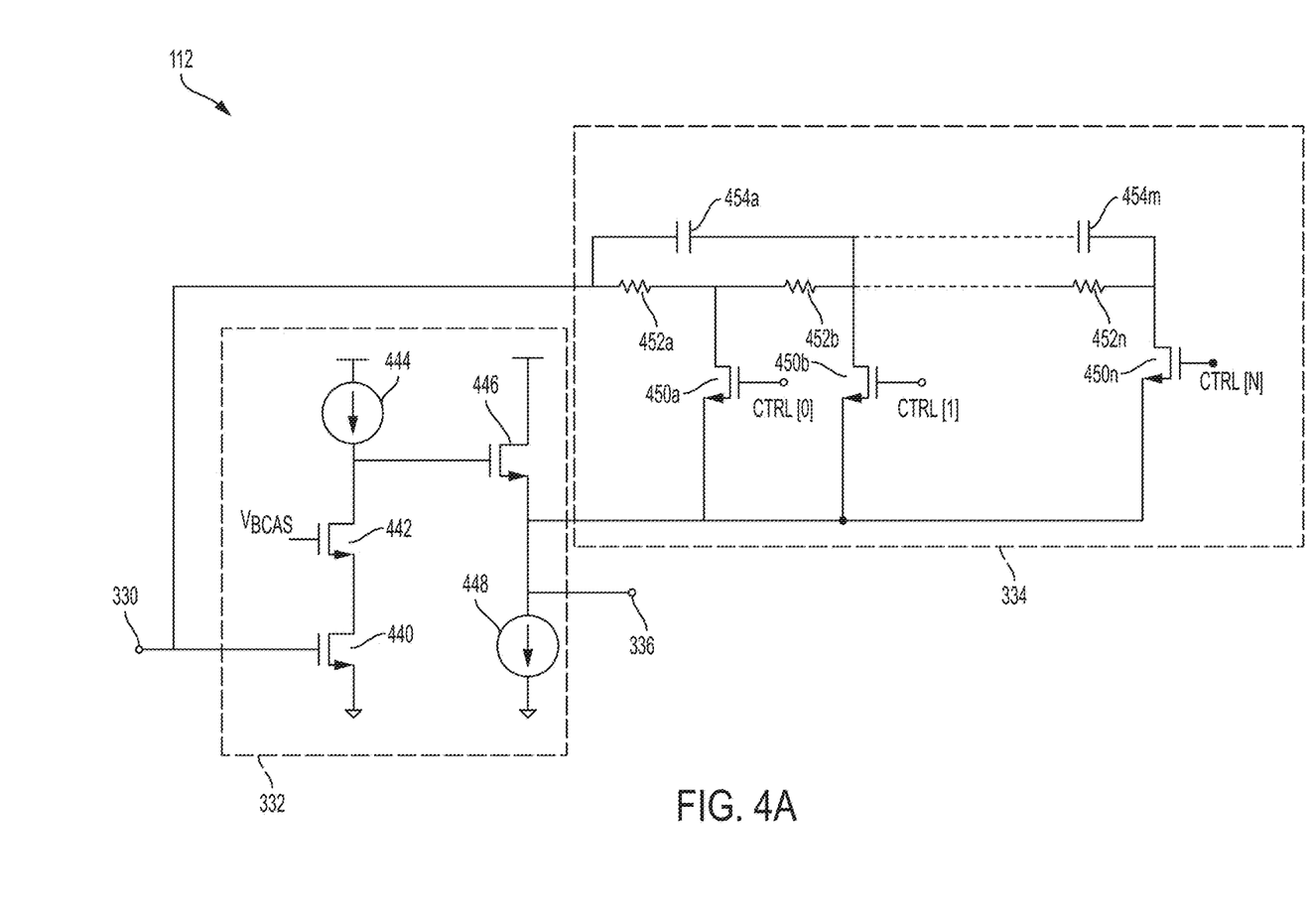
FIG. 4A is a circuit diagram of an implementation of a TIA with TGC functionality, according to a non-limiting embodiment of the present application.

FIG. 4A illustrates a circuit schematic for a TIA with TGC functionality (e.g. one of the amplifiers 112), according to a non-limiting embodiment of the present application. FIG. 4A includes input terminal 330, amplifier 332, variable impedance feedback circuit 334, and output terminal 336. Amplifier 332 includes an NMOS transistor 440, NMOS transistor 442, current source 444, PMOS transistor 446, and current source 448. Variable impedance feedback circuit 334 includes a number, N, of NMOS transistors 450a ... 450n configured to receive N respective control signals CTRL[0] ... CTRL[N], a number, N, of resistors 452a ... 452n, and a number, M, of capacitors 454a ... 454m.

An analog electrical signal from an ultrasound transducer is received at the input terminal 330. The input is connected to the gate of the NMOS transistor 440, the source being connected to ground and the drain being connected to the NMOS transistor 442. The gate of the NMOS transistor 442 is connected to a bias voltage that may be configured to change the gain of the amplifier. In some implementations, the NMOS transistor 442 is omitted and NMOS transistor 440 is directly coupled to the current source 444. In some implementations, current source 444 may be implemented using one or more transistors (e.g., one, two, or more PMOS transistors), not shown in FIG. 4A. Current source 444 may be implemented using any suitable current source circuitry.

The gate of the NMOS transistor 446 is connected to the output of the current source 444 and the drain of the NMOS transistor 442. The drain of NMOS transistor 446 is connected to a positive power supply voltage, and the source of NMOS transistor 446 is connected to current source 448, the output 336, and the variable impedance feedback circuit 334. The current source 448 may be implemented as one or more transistors, a resistor, or any suitable circuitry.

The variable impedance feedback circuit 334 is coupled to the output terminal 336 and the input terminal 330. The variable impedance feedback circuit 334 receives the N control signals, CTRL[0], CTRL[1] ... CTRL[N], at the NMOS transistors 450a ... 450n that are used to configure the impedance of the feedback path from the output 336 to the input 330. When the control signal CTRL[0] is high, a logical one, the NMOS transistor 450a completes a feedback path, from the output terminal 336 to the input terminal 330, that includes resistor 452a. When the control signal CTRL[0] is low, a logical zero, the NMOS transistor 450a breaks the feedback path. If CTRL[1] is asserted high while CTRL[0] is low, the NMOS transistor 450b completes a feedback path, from the output terminal 336 to the input terminal 330, that includes the resistor 452b and the resistor 452a, which has increased impedance relative to the feedback path with the resistor 452a as the sole resistor. In this manner, the amplifier gain may be increased.

The resistors 452a ... 452n may have any suitable relationship to provide varying gain. For example, in some implementations, the resistors 452a ... 452n provide resistance values that change sequentially from resistor 452a to resistor 452n. In some implementations, the resistors 452a ... 452n are sized so that adding an additional resistor to the feedback path, e.g. by switching off a first transistor of the NMOS transistors 450a ... 450n and switching on a second one of the NMOS transistors 450a ... 450n that is adjacent to the first transistor and closer to the Nth transistor, creates a logarithmically scaled increase in the gain of the amplifier 112. For example, the resistor 452a may be sized to provide 90 dB of gain and each resistor that is added to the feedback path may subsequently, may increase the gain by one decibel. In some implementations, the resistance of each resistor of the resistors 452a ... 452n or a subset of the resistors 452*a* . . . 452*n* is scaled by a constant scaling factor, e.g., each resistor in a subset of the resistors 452*a* . . . 452*n* has 10%, 20%, 30%, or more resistance than the adjacent resistor more proximate to the input 330. In some implementations, the resistance of one or more (e.g., each) resistors is scaled so that the characteristic RC time constant of the variable impedance feedback circuit 334 is scaled by a constant factor with each additional resistor on the feedback path. Configuring the resistors in any of the manners describe may facilitate providing variable gain, and thus achieving TGC functionality.

The capacitor 454*a* is shown connected in parallel with the resistors 452*a* and 452*b*. In some implementations, there may be one capacitor for each grouping of resistor, transistor, and control signal. For example, in some embodiments the number of capacitors M is equal to the number of resistors N. In some implementations, each capacitor is in parallel with one or more resistors. For example, each capacitor may be in parallel with two resistors and M may be one half of N. The capacitors 454*a* . . . 454*m* may be sized and arranged with one or more resistors each to address various designs concerns, such as area, cost, and bandwidth, without departing from the scope of the present application.

Figure 4B:
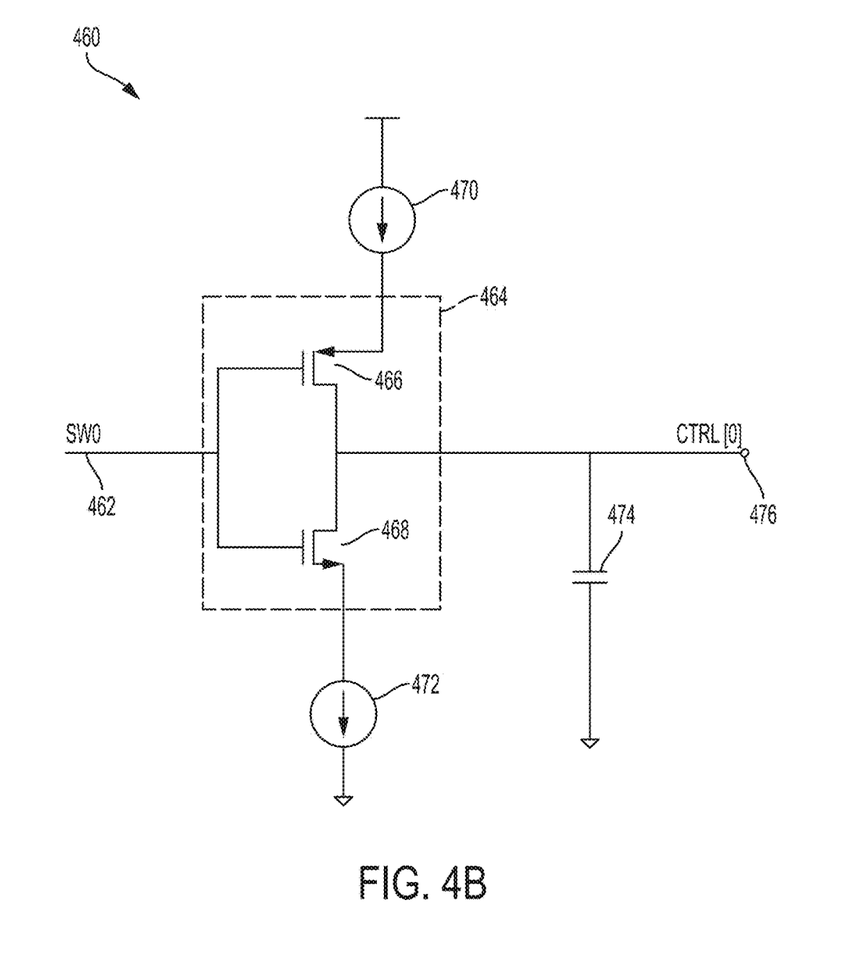
FIG. 4B is a circuit diagram of an implementation of a TGC control signal switching circuit, according to a non-limiting embodiment of the present application.

FIG. 4B illustrates a circuit schematic for a TGC control signal switching circuit, charge pump circuit 460, according to a non-limiting embodiment of the present application. FIG. 4B includes switch signal input 462, switch 464, current source 470, current source 472, capacitor 474, and control signal output 476. To activate or deactive a given control signal, e.g., one of CTRL[0] . . . CTRL[N] discussed with reference to FIG. 4A, a switching signal, SW0, is received at the switch signal input 462. The switch 464 includes PMOS transistor 466 and NMOS transistor 468, which both have respective gates connected to receive the switch signal input 462. The PMOS transistor 466 and the NMOS transistor 468 are shown in an inverter arrangement, such that the control signal output 476 will be the logical opposite of switch signal input 462. However, any suitable switching means may be used in the switch 464.

The output of the switch 464 is connected to the capacitor 474, which is configured to slow the edges of control signal output 476 during transitions between logic levels. Since the ultrasound transducer is receiving a continuous signal, abrupt changes in the control signal, and therefore the gain of amplifier 112*a* (or any of amplifiers 112*b* . . . 112*n*), could create transient errors, such as a glitch, in the ultrasound measurements. By slowing the transitions between logic level for the control signal output 476, capacitor 474 can prevent, reduce, and/or substantially eliminate transient switching errors from the ultrasound measurements such that the impact to the ultrasound measurement of altering the gain of amplifier 112 is dominated by the desired increase in gain and switching errors are comparatively negligible.

During transitions from low to high output, the capacitor charges and slows the rise time of the output. During transitions from high to low output, the capacitor discharges over time to slow the transition. A maximum transition time for the output may be specified to achieve a sufficiently rapid rate of TGC control transitions, e.g. 0.005 dB per 10 nanoseconds, 0.01 dB per 10 nanoseconds, 0.01 dB per nanosecond, 0.1 dB per nanosecond, or 0.2 dB per nanosecond or any other suitable value. It should be appreciated that the transition profile (gain/attenuation curve) determined by the amplifier 112 and TGC circuitry (e.g. 334 and 460) should be present in the digital domain after digitization by the ADC (e.g. 126). Due to the physics of the circuitry involved, the digitized transition profile may differ from an ideal or target transition profile, and the differences between the actual and target profiles may be corrected in the digital domain, for example, by modeling the gain circuitry and applying a digital gain configured to eliminate the discrepancy. In some implementations, adjustments are made to the digital signal based on a model of the gain circuitry, e.g. a model of the transitions between levels of impedance feedback used to increase the gain, and not based on any specific, desired gain/attenuation curve.

Capacitor 474 may be any suitably sized capacitor. For example, the capacitor may have a size of 100 femtofarads, 200 femtofarads, 500 femtofarads, 1 picofarad, or any other suitable capacitance value. In some implementations, capacitor 474 may be implemented using multiple capacitors arranged in an array. In some implementations, the amount of capacitance may be dynamically switched using control signals or otherwise configurable or programmable, e.g. by using transistors to connect each transistor in the array to the control signal output 476. The amount of capacitance connected between ground and control signal output 476 can be varied to control the slew rate of the amplifier and TGC, depending on the amount of glitch error energy that can be tolerated in the measurements. For example, smaller capacitance values may be selected from an array of capacitors when rapid TGC operation is required and relatively high levels of glitch energy can be tolerated. Alternatively, other circuitry may be implemented to store and release electrical charge—in sufficient quantities and for sufficient durations—to avoid having the control signal transitions introduce transient errors that would degrade the ultrasound readings.

Figure 4C:
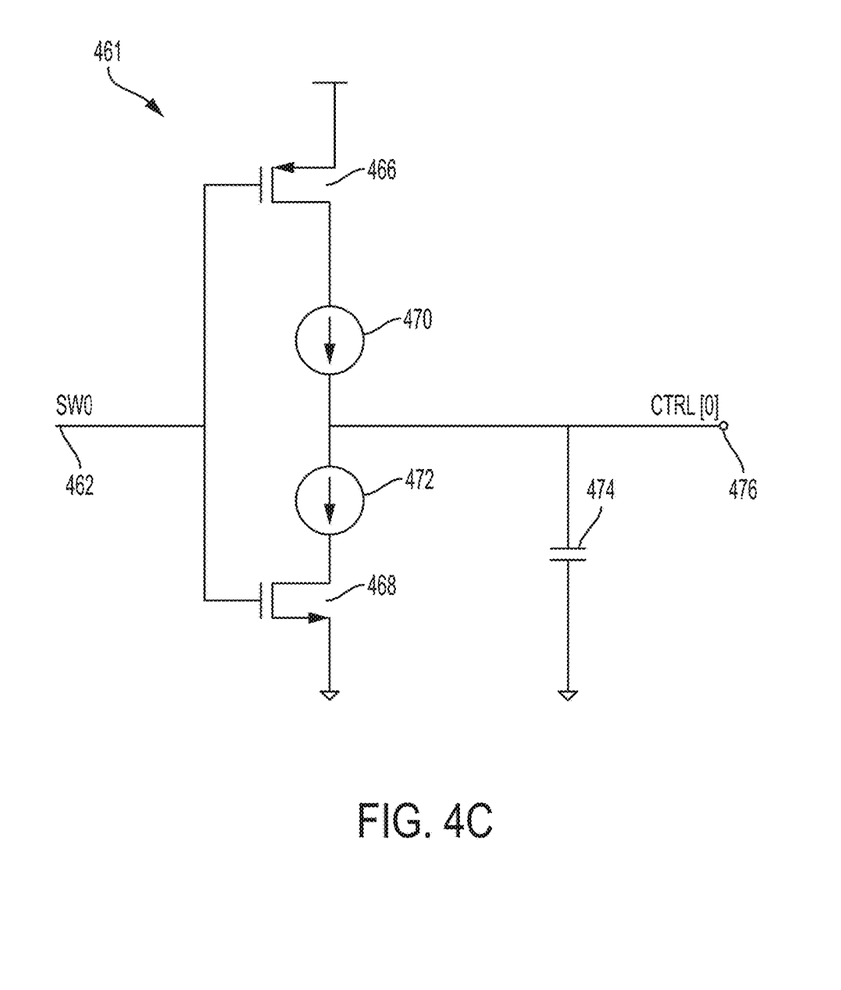
FIG. 4C is a circuit diagram of an implementation of a TGC control signal switching circuit, according to a non-limiting embodiment of the present application.

FIG. 4C illustrates a circuit schematic for a TGC control signal switching circuit, charge pump circuit 461 according to a non-limiting embodiment of the present application. FIG. 4C includes the same components as the charge pump circuit of FIG. 4B but arranged differently. Thus, charge pump circuit 461 includes switch signal input 462, PMOS transistor 466, NMOS transistor 468, current source 470, current source 472, capacitor 474, and control signal output 476. To activate or deactive a given control signal, e.g., one of CTRL[0] . . . CTRL[N] discussed with reference to FIG. 4A, a switching signal, SW0, is received at the switch signal input 462. PMOS transistor 466 and NMOS transistor 468, which were discussed with reference to switch 464 in FIG. 43, both have respective gates connected to receive the switch signal input 462. The PMOS transistor 466 and the NMOS transistor 468 are shown in an inverter arrangement, such that the control signal output 476 will be the logical opposite of switch signal input 462. However, any suitable switching means may be used to switch the transistors 466 and 468. The circuit schematic of FIG. 4C differs from the schematic of FIG. 4B by depicting current source 470 and current source 472 as being between PMOS transistor 466 and NMOS transistor 468. It should be understood that charge pump 461 may be implemented using a variety of circuit arrangements that are capable of controlling the rate of rise and fall of the control signal outputs (e.g. 476) such that the changes are slow enough to substantially reduce or eliminate glitch errors but rapid enough to provide a sufficiently high amplifier slew rate.

Figure 4D:
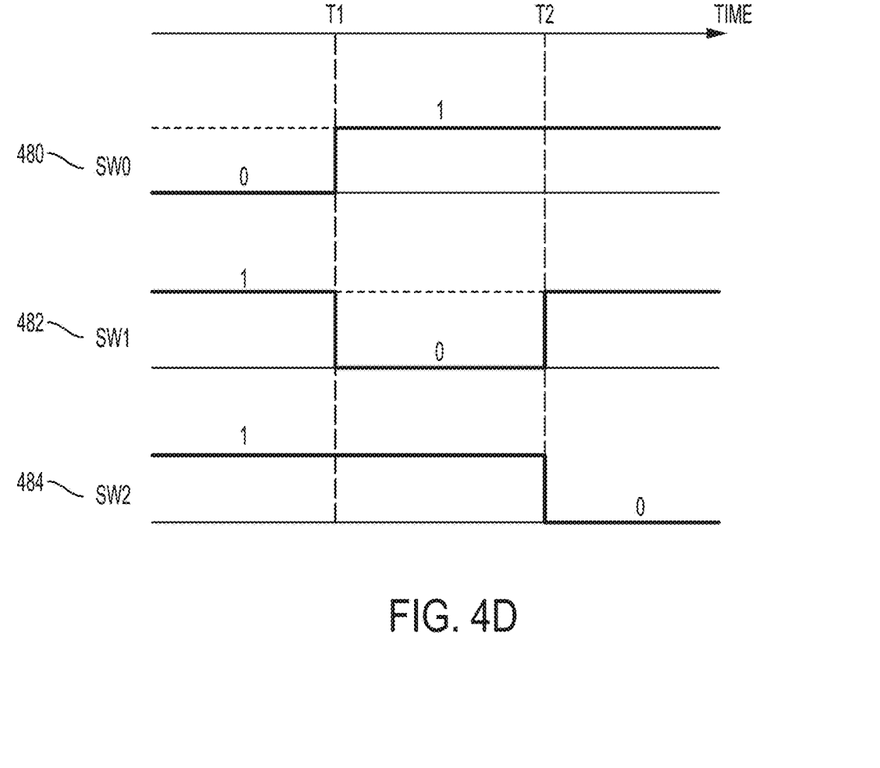
FIG. 4D illustrates an exemplary operating sequence for TGC control signals, according to a non-limiting embodiment of the present application.

FIG. 4D illustrates an exemplary operating sequence for TGC control signals, according to a non-limiting embodiment of the present application. FIG, 4l) shows the time variation of three control signal switching signals, SW0 signal 480, SW1 signal 482, and SW2 signal 484. The switching signals 480, 482, 484 may be generated by a microcontroller, timing circuitry, a processor, or any other suitable control circuitry. In some implementations, one or more (e.g., each) of the switching signals has a respective, corresponding control signal. For example, the SW0 signal may correspond to the CTRL[0] signal discussed with reference to FIGS. 4A and 4B, the SW1 signal may correspond the CTRL[1] signal, and the SW2 signal may correspond to a CTRL[2] signal or the CTRL[N] signal Initially, the SW0 signal 480 is a logical zero (a low signal that may be equivalent to ground), while the other signals are logical ones (high signals that may be equivalent to the supply voltage). When output to the TGC control signal switching circuit 460 discussed with reference to FIG. 4B, a logically low SW0 switch signal will cause the corresponding CTRL[0] control signal to be asserted as logically one, which in turn opens a feedback path as discussed with reference to FIG. 4A. In this example, having only the SW0 signal 480 logically zero creates a single resistor feedback path and activates the lowest gain setting in the amplifier 112. At time Ti, the SW0 signal 480 is switched to a logical one, e.g., as discussed with reference to FIG. 4B, and the SW1 signal 482 is switched to a logical zero, while the SW2 signal 484 remains logically one. This increases the resistance of the exemplary variable impedance feedback circuit 334 as discussed with reference to FIG. 4A and, thereby, increases the gain of the amplifier 112. At a time T2 that is later than time T1, the SW0 signal 480 remains logically one, the SW1 signal 482 is switched from logical zero to logical one, and the SW2 signal 484 is switched from logical one to logical zero, thereby further increasing the impedance of variable impedance feedback circuit 334 and further increasing the gain of the amplifier 112. This sequence of temporally, sequentially increasing gain provides TGC functionality to the amplifier 112.

It should be appreciated that the sequence illustrated in FIG. 4D is non-limiting. For example, the number of time periods and switching signals shown are not limiting. In some implementations, multiple switching signals and corresponding control signals may be asserted high or low at a given time, e.g., to permit for different arrangements of switching and variable impedance circuitry or to allow for more fine grained control of the impedance and gain than is allowed by a series arrangement of resistors.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described. For example, while several embodiments have been described as employing a TIA, other amplifiers may alternatively be used, including LNAs and trans-conductance amplifiers. More generally, voltage amplifiers may be implemented, and may be beneficial when the ultrasound device includes a transducer which outputs a voltage signal, such as a piezoelectric crystal transducer. Other variations are possible.

As described, some aspects may be embodied as one or more methods. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements.

As used herein, the term "between" used in a numerical context is to be inclusive unless indicated otherwise. For example, "between A and B" includes A and B unless indicated otherwise.

In the claims, as well as in the specification above, all transitional phrases such as "comprising," "including," "carrying," "having," "containing," "involving," "holding," "composed of" and the like are to be understood to be open-ended. i.e., to mean including but not limited to. Only the transitional phrases "consisting of" and "consisting essentially of" shall be closed or semi-closed transitional phrases, respectively.

The invention claimed is:

1. An ultrasound apparatus, comprising:
   an ultrasonic transducer to provide an analog electrical signal;
   an amplifier having time gain compensation (TGC) functionality coupled to the ultrasonic transducer and configured to receive and amplify the analog electrical signal by a time-dependent amount;
   wherein:
   the amplifier comprises amplification circuitry and feedback circuitry with a variable impedance; and
   the feedback circuitry comprises a plurality of resistors in a series arrangement, and wherein a subset of the plurality of resistors have respective resistance values that increase sequentially in a logarithmic fashion.

2. The ultrasound apparatus of claim 1, wherein the amplifier is a trans-impedance amplifier (TIA).

3. The ultrasound apparatus of claim 1, wherein the amplifier is a trans-conductance amplifier.

4. The ultrasound apparatus of claim 1, wherein the amplifier is a low noise amplifier (LNA).

5. The ultrasound apparatus of claim 1, wherein the ultrasonic transducer is a first ultrasonic transducer and the amplifier is a first amplifier, the ultrasound apparatus comprising a plurality of ultrasonic transducers including the first ultrasonic transducer and a plurality of respective amplifiers coupled to the respective ultrasonic transducers, the plurality of respective amplifiers including the first amplifier, wherein the ultrasound apparatus further comprises an averaging circuit coupled to the plurality of respective amplifiers.

6. The ultrasound apparatus of claim 5, wherein the averaging circuit comprises TGC circuitry distinct from the TGC functionality of the amplifier.

7. The ultrasound apparatus of claim 1, wherein the ultrasonic transducer and the amplifier are integrated on a same substrate to form an integrated electronic device.

8. The ultrasound apparatus of claim 1, wherein the amplifier is configured to receive a plurality of control signals, and wherein the time-dependent amount of gain is determined based on at least one control signal of the plurality of control signals.

9. The ultrasound apparatus of claim 8, wherein the at east one control signal represents a signal from a charge pump.

10. The ultrasound apparatus of claim 9, wherein the charge pump comprises a capacitor.

11. The ultrasound apparatus of claim 1, wherein the analog electrical signal comprises ultrasound image data.

12. The ultrasound apparatus of claim 1, further comprising a switch coupled between the ultrasonic transducer and the amplifier.

13. An ultrasound circuit, comprising:
an ultrasonic transducer;
an analog signal processing chain coupled to the ultrasonic transducer; and
an analog-to-digital converter (ADC), wherein the analog signal processing chain is coupled electrically between the ultrasonic transducer and the ADC, wherein the analog signal processing chain includes a combined trans-impedance amplifier (TIA) and time gain compensation (TGC) circuit; and
a plurality of ultrasonic transducers including the ultrasonic transducer and a plurality of respective combined TIA and TGC circuits coupled to respective ultrasonic transducers, the plurality of respective combined TIA and TGC circuits including the combined TIA and TGC circuit, wherein the ultrasound apparatus further comprises an averaging circuit coupled to the plurality of respective combined TIA and TGC circuits.

14. The ultrasound circuit of claim 13, wherein the analog signal processing chain lacks a distinct TGC circuit between the combined TIA and TGC circuit and the ADC.

15. The ultrasound circuit of claim 13, further comprising a switch coupled between the ultrasonic transducer and the combined TIA and TGC circuit.

16. The ultrasound circuit of claim 13, wherein the averaging circuit comprises a TGC circuit.

17. The ultrasound circuit of claim 13, wherein the combined TIA and TGC circuit is configured to apply a time varying amount of gain to an analog electrical signal from the ultrasonic transducer.

18. The ultrasound circuit of claim 17, wherein the combined TIA and TGC circuit is configured to receive a plurality of control signals determining a magnitude of the time varying amount of gain.

19. The ultrasound system of claim 18, further comprising charge pump circuitry configured to delay logic level transitions of at least one control signal of the plurality of control signals.

20. The ultrasound circuit of claim 18, further comprising switching circuitry configured to receive a plurality of switching signals, the switching circuitry configured to assert the plurality of control signals in a sequential order.

21. The ultrasound circuit of claim 18, further comprising selectable resistive segments configured to be selected by the plurality of control signals to increase the magnitude of the time varying amount of gain by logarithmically scaled increments.

* * * * *

UNITED STATES PATENT AND TRADEMARK OFFICE
CERTIFICATE OF CORRECTION

PATENT NO. : 10,340,867 B2
APPLICATION NO. : 16/245202
DATED : July 2, 2019
INVENTOR(S) : Amandeep Singh et al.

It is certified that error appears in the above-identified patent and that said Letters Patent is hereby corrected as shown below:

In the Claims

At Column 11, Claim 9, Line 6, please delete the word "east" and replace it with --least--.

Signed and Sealed this
Twenty-ninth Day of October, 2019

Andrei Iancu
*Director of the United States Patent and Trademark Office*